US012691244B2

(12) United States Patent
Roy

(10) Patent No.: US 12,691,244 B2
(45) Date of Patent: Jul. 28, 2026

(54) DEVICE AND PROCESS FOR EXTENDING A VENTILATOR CIRCUIT

(71) Applicant: Convergence Medical Sciences Ltd., Calgary (CA)

(72) Inventor: Steven Daniel Roy, Calgary (CA)

(73) Assignee: Convergence Medical Sciences Ltd., Calgary (CA)

( * ) Notice: Subject to any disclaimer, the term of this patent is extended or adjusted under 35 U.S.C. 154(b) by 961 days.

(21) Appl. No.: 18/045,581

(22) Filed: Oct. 11, 2022

(65) Prior Publication Data

US 2023/0057019 A1      Feb. 23, 2023

Related U.S. Application Data

(63) Continuation of application No. PCT/CA2021/051519, filed on Oct. 28, 2021.

(60) Provisional application No. 63/107,662, filed on Oct. 30, 2020.

(51) Int. Cl.
*A61M 16/08* (2006.01)
*A61M 16/00* (2006.01)
*A61M 16/20* (2006.01)

(52) U.S. Cl.
CPC ...... *A61M 16/0883* (2014.02); *A61M 16/201* (2014.02); *A61M 16/208* (2013.01); *A61M 2016/0027* (2013.01); *A61M 16/0833* (2014.02); *A61M 16/204* (2014.02); *A61M 16/205* (2014.02); *A61M 2205/11* (2013.01); *A61M 2205/84* (2013.01)

(58) Field of Classification Search
CPC ........... A62B 9/02; A62B 9/04; A61M 16/08; A61M 16/20; A61M 2205/84
See application file for complete search history.

(56) References Cited

U.S. PATENT DOCUMENTS

| | | | |
|---|---|---|---|
| 6,776,158 B1 | 8/2004 | Anderson et al. | |
| 7,721,736 B2 | 5/2010 | Urias et al. | |
| 8,225,788 B2 * | 7/2012 | Manigel ................ | A61M 16/01 128/205.27 |
| 2003/0015199 A1 | 1/2003 | Fuhrman et al. | |
| 2004/0035424 A1 | 2/2004 | Wiesmann et al. | |

(Continued)

FOREIGN PATENT DOCUMENTS

| | | | |
|---|---|---|---|
| WO | 2012045560 | 4/2012 | |
| WO | WO-2012045560 A2 * | 4/2012 | ............. A61B 5/097 |

OTHER PUBLICATIONS

Roy et al., Inline Positive End-Expiratory Pressure Valves: The Essential Component of Individualized Split Ventilator Circuits, Critical Care Explorations, 2020, 6 pages, vol. 2, USA.

(Continued)

*Primary Examiner* — Brandy S Lee
*Assistant Examiner* — Mishal Zahra Hussain
(74) *Attorney, Agent, or Firm* — Heslin Rothenberg Farley & Mesiti P.C.

(57)            ABSTRACT

A device for enclosing a positive end valve (PEEP valve) and converting the PEEP valve to an inline valve for use in a differential multi-ventilation system is described. The device includes a housing configured to enclose the PEEP valve. The housing also includes a ventilator-side arm, a pass-through arm and a patient-side arm. The pass-through arm permits extension of the multi-ventilation system to add one or more patients to the system.

23 Claims, 8 Drawing Sheets

(56)           References Cited

U.S. PATENT DOCUMENTS

| | | | |
|---|---|---|---|
| 2005/0040646 A1 | 2/2005 | Brumfield et al. | |
| 2006/0189880 A1 | 8/2006 | Lynn et al. | |
| 2009/0050151 A1* | 2/2009 | Fuhrman ........... | A61M 16/0084 |
| | | | 128/205.12 |
| 2012/0012111 A1* | 1/2012 | Howe, Jr. ......... | A61M 16/1055 |
| | | | 128/205.12 |
| 2012/0283592 A1* | 11/2012 | Schuessler ........ | A61M 16/0006 |
| | | | 128/204.23 |
| 2013/0098363 A1* | 4/2013 | Forte ................. | A61M 16/0434 |
| | | | 128/204.23 |
| 2017/0128693 A1* | 5/2017 | Darowski ........... | A61M 16/202 |
| 2021/0299388 A1* | 9/2021 | Vankoevering ....... | A61M 16/20 |
| 2024/0207560 A1* | 6/2024 | Khwaja .............. | A61M 16/024 |

OTHER PUBLICATIONS

International Search Report and Written Opinion of the International Searching Authority for International Application No. PCT/CA2021/051519 mailed on Jan. 18, 2022, 9 pages.

* cited by examiner

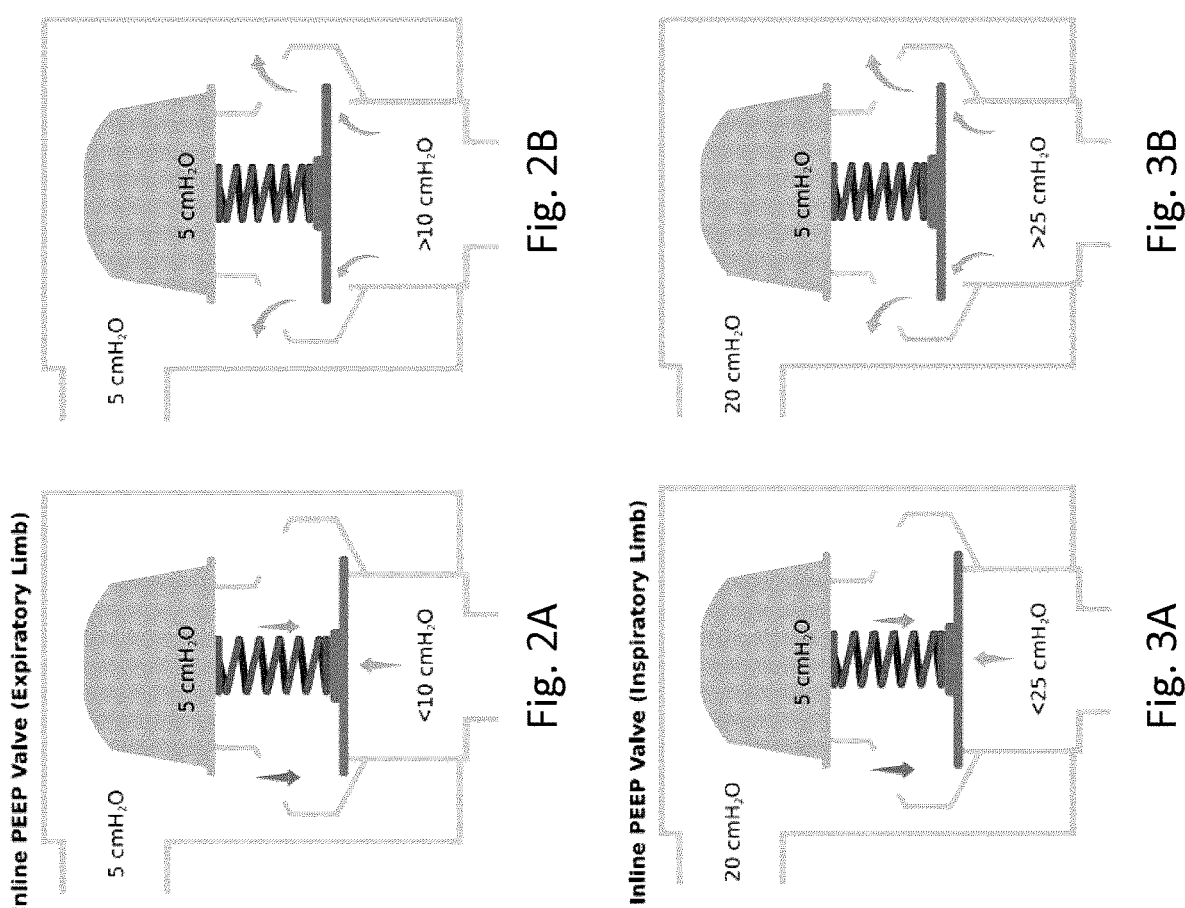

ADJUSTMENT HEAD 503
VENT 505
RETAINING ELEMENT 115
INDICATOR 117
110
112
114
PRESSURE MARKINGS 509
PEEP VALVE 500
VALVE BODY 501
VALVE PORT 507
PRESSURE MARKINGS 116
111
113
100

INSPIRATORY VALVE 100
PASS THROUGH ARM 112
PATIENT ARM 113
EXPIRATORY VALVE 200
PASS THROUGH ARM 212
INDICATOR 217
CAP 230
BASE CONNECTOR 214
CAP 130
HOUSING 110
VENTILATOR ARM 111
BASE CONNECTOR 114
PATIENT ARM 213
VENTILATOR ARM 211
HOUSING 210
PRESSURE MARKINGS 216

SLEEVE
135

503

130

500

100

112

114

111

113

110

TO PATIENT

PATIENT CONDUIT 120

FROM VENTILATOR

PASS THROUGH CONDUIT 113

PASS THROUGH CONDUIT 118

112

115

VALVE CONDUIT 119

MAIN CAVITY 121

INSPIRATORY HOUSING 110

111

PASS THROUGH CONDUIT 218

FROM PATIENT

213

VALVE CONDUIT 219

215

211

TO VENTILATOR

212

PATIENT CONDUIT 220

MAIN CAVITY 221

EXPIRATORY HOUSING 210

500

503

115

501

505

111

110

112

113

DEVICE AND PROCESS FOR EXTENDING A VENTILATOR CIRCUIT

CROSS REFERENCE TO RELATED APPLICATION

This application is a Bypass Continuation Application to PCT International Application No. PCT/CA2021/051509, filed Oct. 28, 2021, and entitled "Device and Process for Extending a Ventilator Circuit", which claims priority benefit under 35 U.S.C. § 119(e) of U.S. Provisional Patent Application No. 63/107,662, filed Oct. 30, 2020, both applications and the disclosures of each are hereby incorporated herein by reference in their entirety.

TECHNICAL FIELD

The technology relates to systems for providing mechanical ventilation in a medical setting and more specifically to a device used to house in-line valves used in ventilator circuits.

BACKGROUND

A ventilator is a machine that provides mechanical ventilation by moving breathable air into and out of the lungs, to deliver breaths to a patient who is physically unable to breathe, or breathing insufficiently. Modern ventilators are computerized microprocessor-controlled machines. Patients can also be ventilated with a simple, hand-operated bag valve mask. Ventilators are mostly used in intensive-care medicine, home care, and emergency medicine (as standalone units), in transporting patients for critical care or prehospital emergency medical services and in anesthesiology (as a component of an anesthesia machine).

In its simplest form, a modern positive pressure ventilator consists of a compressible air reservoir or turbine, air and oxygen supplies, a set of valves and tubes, and a disposable or reusable "patient circuit." The air reservoir is pneumatically compressed several times a minute to deliver room-air or, in most cases, an air/oxygen mixture to the patient. If a turbine is used, the turbine pushes air through the ventilator, with a flow valve adjusting pressure to meet patient-specific parameters. When over pressure is released, the patient will exhale passively due to the lungs' elasticity, the exhaled air being released usually through a one-way valve within the patient circuit known as the patient manifold.

Modern conventional ventilators are usually equipped with monitoring and alarm systems for patient-related parameters (e.g., pressure, volume, and flow) and ventilator function (e.g., air leakage, power failure, mechanical failure), backup batteries, oxygen tanks, and remote control. The pneumatic system is often replaced by a computer-controlled turbopump.

Modern ventilators are electronically controlled by a small embedded system to allow exact adaptation of pressure and flow characteristics to an individual patient's needs. Fine-tuned ventilator settings also serve to make ventilation more tolerable and comfortable for the patient. The patient circuit usually consists of a set of three durable, yet lightweight plastic tubes, separated by function (e.g., inhaled air, patient pressure, exhaled air). Determined by the type of ventilation needed, the patient-end of the circuit may be either noninvasive or invasive.

As resources are overwhelmed with the coronavirus disease 2019 pandemic and ventilator shortages occur or are envisioned, health systems have been scrambling for methods for increasing ventilator capacity. One solution that has been proposed is to share ventilators between multiple patients. Although so-called "co-ventilation" strategies have been used in New York and have received crisis approval by US agencies including Health and Human Services and the Federal Drug Administration, there are major potential risks with such approaches, and major medical organizations have made statements against their use. To address these limitations, several international working groups have designed modified ventilator circuits which permit individualized settings for patients sharing a ventilator. These modified systems, which are known as differential multi-ventilation systems, use flow restrictors and sensors to allow discrete adjustment and monitoring of inspiratory and expiratory variables. An example system is shown in (Roy et al, 2020, Crit. Care Explor. 2(9): e0198, incorporated herein by reference in its entirety).

Most differential multi-ventilation systems use variations on a fundamental approach in attempts to solve the challenges associated with split-ventilators. First, because patient triggering of the ventilator could lead to overventilation of one or both patients and potentially dangerous patient-patient-ventilator interactions, all patients must be passively ventilated. Adequate sedation and, if necessary, paralytics are used to prevent one or more patients from triggering breaths. Second, the ventilator must be in a pressure control mode. Using a pressure-regulated ventilator mode prevents the situation where a single patient receives the tidal volume intended for two or more patients if a circuit or patient obstructs. As a secondary benefit, pressure-based modes also facilitate the individualization process since pressure is easier to mechanically regulate than volume. Third, patient ventilation variables are individually monitored using digital or mechanical pressure manometry, flow sensors, end-tidal $CO_2$ monitors, and/or noninvasive cardiac output monitors. Finally, valves and flow restrictors are used in each patient's circuit to individualize ventilator variables. Although many flow restrictors have been described, most differential multi-ventilation systems use adjustable inline positive end-expiratory pressure (PEEP) valves in at least some part of the system. Inline PEEP valves serve three key functions in differential multi-ventilation systems: 1) reducing delivered peak inspiratory pressure (PIP) to an individual patient circuit (flow restrictor); 2) increasing PEEP for an individual patient circuit (pressure release valve); and 3) acting as one-way valves (also known as check valves) to ensure unidirectional gas flow through the divided circuit.

Under normal circumstances, the pressure in the lung at the end of expiration is equal to the atmospheric pressure. PEEP refers to the application of additional pressure at the end of expiration to maintain pressure in the lung slightly above atmospheric pressure. This pressure trapped inside the lungs acts as a force pushing outward on the alveoli and holding them open. It increases the volume of gas inside the lung at the end of expiration. PEEP is a simple basic setting on most mechanical ventilators.

There remains a need for improvements in differential multi-ventilation systems.

SUMMARY

According to one aspect of the technology, there is provided a device for enclosing a positive end valve (PEEP valve) and converting the PEEP valve to an inline valve for use in a differential multi-ventilation system. In one embodiment, the device includes a housing configured to enclose the PEEP valve. The housing includes a ventilator-side arm, a pass-through arm and a patient-side arm. The pass-through arm permitting extension of the multi-ventilation system to add one or more patient circuits to the system.

The ventilator-side arm and the pass-through arm may be dimensioned for direct connection to each other such that the pass-through arm of a first device as described above is connectable to the ventilator-side arm of a second device as described above.

The device may be configured for use as an inspiratory inline valve, wherein the ventilator-side arm together with the pass-through arm are co-axial with a first conduit through the housing. In this arrangement, the first conduit is contiguous with a substantially perpendicular second conduit substantially centralized within the housing and the second conduit configured to connect to a valve port of the PEEP valve when the PEEP valve is installed in the device. In this arrangement, the second conduit is isolated from the patient-side arm when the PEEP valve is installed in the device and the PEEP valve is closed, and the second conduit permits gas flow to the patient-side arm when the PEEP valve is installed in the device and the PEEP valve is open.

The device may be configured for use as an expiratory inline valve, wherein the patient-side arm is contiguous with a substantially perpendicular second conduit substantially centralized within the housing. In this arrangement, the second conduit is configured to connect to a main sleeve of the PEEP valve when the PEEP valve is installed in the device. In this arrangement, the second conduit is isolated from the ventilator-side arm and the pass-through arm when the PEEP valve is installed in the device and the PEEP valve is closed, and the second conduit permits gas flow to the ventilator-side arm when the PEEP valve is installed in the device and the PEEP valve is open.

In any of the embodiments above, the housing may be defined by a main opening and a cap is coupled to the body over the main opening, the cap having an inner structure configured to connect to a pressure adjustment head of the PEEP valve, thereby permitting the cap to control the pressure adjustment head of the PEEP valve. The inner structure of the cap may include a sleeve dimensioned to couple to the pressure adjustment head of the PEEP valve when the PEEP valve is installed in the device. The cap may be coupled to the housing by threading, wherein the threading permits adjustment of the pressure adjustment head of the PEEP valve.

In some embodiments, an outer sidewall of the housing includes markings indicating valve pressure, wherein positioning of an edge of the cap with respect to the markings indicates the valve pressure according to an extent of the threading.

In some embodiments, an inner sidewall of the housing includes a PEEP-valve retaining element.

According to another aspect of the technology, there is provided a set of devices for assembling and connecting inspiratory and expiratory inline valves to each other. In one embodiment, the set includes an inspiratory device as recited above which further includes a first connector on the body of the inspiratory device, and an expiratory device as recited above which further includes a second connector on the housing of the expiratory device, In this embodiment, the first connector and the second connector are configured to connect to each other.

In some embodiments of the set of devices, the housing of the inspiratory device includes a first visual indicator to indicate inspiration and the housing of the expiratory device includes a second visual indicator to indicate expiration.

According to another aspect of the technology, there is provided a kit which includes the set of devices described above. The kit also includes instructions for assembling a differential multi-ventilator system using the set of devices. In some embodiments, the kit further includes a plurality of PEEP valves.

According to another aspect of the technology, there is provided a ventilator system which includes a ventilator and a set of inline valves formed from devices as recited above and having PEEP valves installed therein. The ventilator-side arms of both the inspiratory device and the expiratory device are connected to the ventilator, the patient-side arms of both the inspiratory device and the expiratory device are connected to a first patient circuit, and a bypass conduit is connected between the pass-through arms of the inspiratory device and the expiratory device.

According to another aspect of the technology, there is provided a differential multi-ventilator system which includes a ventilator and a first set of inline valves formed from devices as described above and having PEEP valves installed therein. The ventilator-side arms of both the inspiratory device and the expiratory device of the first set of inline valves are connected to the ventilator, and the patient-side arms of both the inspiratory device and the expiratory device of the first set of inline valves are connected to a first patient circuit. The system further includes at least a second set of inline valves formed from devices described above and having PEEP valves installed therein. The second set of inline valves is connected to the first set of inline valves, wherein the pass-through arms of the inspiratory device and the expiratory device of the first set of inline valves are connected to the ventilator-side arms of the inspiratory device and the expiratory device of the second set of inline valves and the patient-side arms of both the inspiratory device and the expiratory device of the second set of inline valves are connected to at least a second patient. A bypass conduit is connected between the pass-through arms of the second set of inline valves or connected between the pass-through arms of a final set of inline valves connected after the second set of devices.

According to another aspect of the technology, there is provided a method for assembling a differential multi-ventilator system. The method includes the steps of: constructing a plurality of sets of inline valves by installing PEEP valves in a plurality of inspiratory devices and expiratory devices as described above; connecting a first set of inline valves of the plurality of inline valves to a ventilator via the ventilator-side arm of the inspiratory device and the ventilator-side arm of the expiratory device of the first set of devices and connecting a first patient circuit to the patient-side arms of the first set of inline valves; connecting at least a second set of inline valves to the first set of inline valves by connecting the pass-through arm of the inspiratory device of the first set of inline valves to the ventilator-side arm of the second set of inline valves and connecting at least a second patient circuit to the patient-side arms of the second set of inline valves; thereby providing an extended set of inline valves; and connecting a bypass conduit between the pass-through arms of a final set of inline valves in the extended set of inline valves.

In some embodiments of the method described above, the extended set of inline valves includes for example, 2, 3, 4, 5 or 6 sets of inline valves.

In some embodiments of the method described above, for each set of inline valves of the extended set of inline valves, the inspiratory device is connected to the expiratory device by making a connection between the first connector and the second connector.

In some embodiments, the method further includes removing the bypass conduit from the final set of inline valves, connecting an additional set of inline valves to the final set of inline valves and connecting the bypass conduit between the pass-through arms of the additional set of inline valves, thereby adding the additional set of inline valves to the extended set of inline valves.

In some embodiments of the method, the ventilator is retained in continuous operation and the first patient circuit continues to operate during the step of connecting at least a second set of inline valves.

BRIEF DESCRIPTION OF THE DRAWINGS

Various objects, features and advantages of the technology will be apparent from the following description of particular embodiments of the technology, as illustrated in the accompanying drawings. The drawings are not necessarily to scale, emphasis instead being placed upon illustrating the principles of various embodiments of the technology. Similar reference numerals indicate similar components.

FIG. 2A is an illustration of an inline (enclosed) PEEP valve of the expiratory limb of a differential multi-ventilation system, with the PEEP valve in the closed position, where air pressure less than 10 cm $H_2O$ does not open the spring valve, in accordance with an aspect of the present invention;

FIG. 2B is an illustration of an inline (enclosed) PEEP valve of the expiratory limb of a differential multi-ventilation system, with the PEEP valve in the open position wherein air pressure greater than 10 cm $H_2O$ opens the spring valve and air enters the enclosure, in accordance with an aspect of the present invention;

FIG. 3A is an illustration of an inline (enclosed) PEEP valve of the inspiratory limb of a differential multi-ventilation system, with the PEEP valve in the closed position, where air pressure less than 25 cm $H_2O$ does not open the spring valve, in accordance with an aspect of the present invention;

FIG. 3B is an illustration of an inline (enclosed) PEEP valve of the inspiratory limb of a differential multi-ventilation system, with the PEEP valve in the open position wherein air pressure greater than 25 cm $H_2O$ opens the spring valve and air enters the enclosure, in accordance with an aspect of the present invention;

DETAILED DESCRIPTION FOR CARRYING OUT THE INVENTION

Figures 1A, 1B:
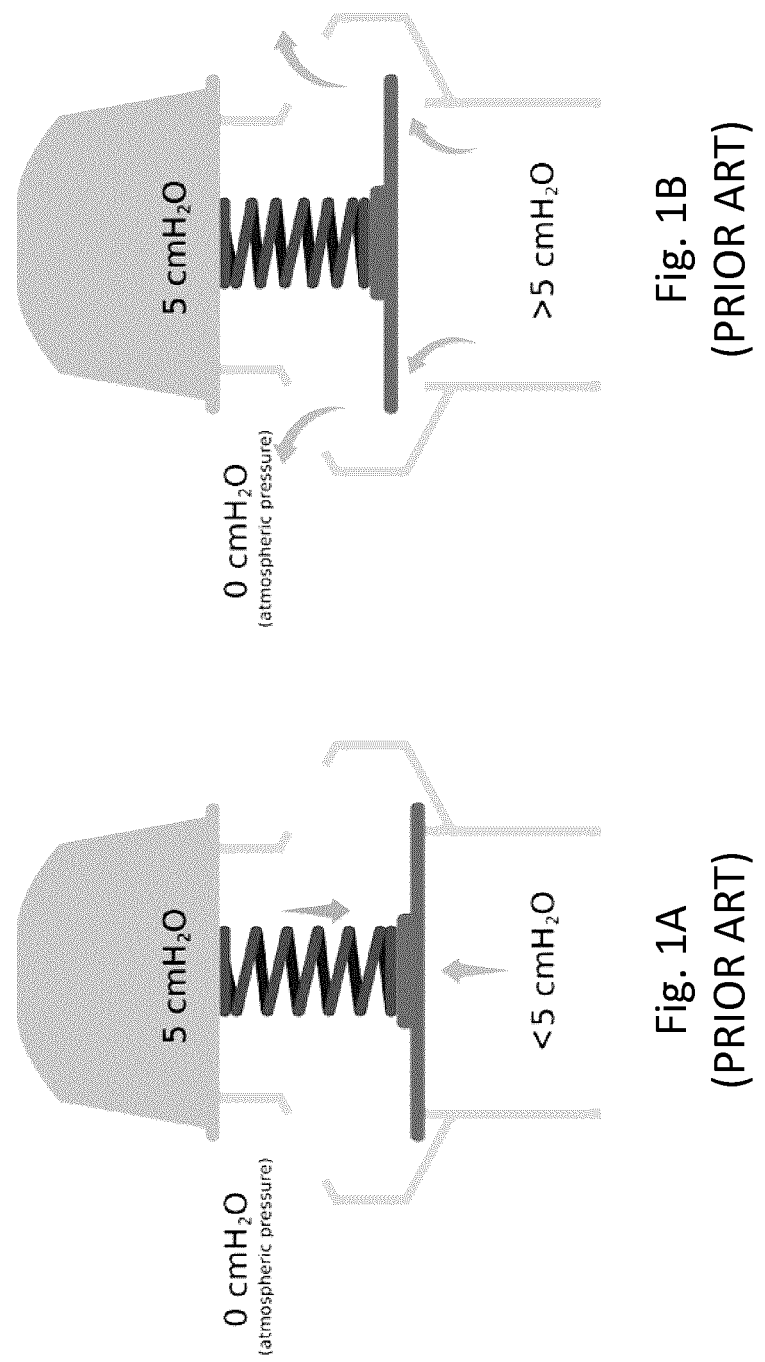
FIG. 1A is an illustration of a conventional PEEP valve in the closed position, where air pressure less than 5 cm $H_2O$ does not open the spring valve, in accordance with an aspect of the present invention.
FIG. 1B is an illustration of a conventional PEEP valve in the open position where air pressure greater than 5 cm $H_2O$ opens the spring valve and air vents to the atmosphere, in accordance with an aspect of the present invention.

Basic Function of the Adjustable PEEP Valves as Pressure Release Valves—PEEP valves are adjustable pressure release valves. They are commonly used in conjunction with bag valve masks and normally vent exhaled gases to the atmosphere. When the pre-valve pressure exceeds the valve setpoint, a diaphragm opens and allows flow. When pre-valve pressure drops below the valve setpoint, the diaphragm closes and flow across the valve stops. Inline PEEP valves additionally function as one-way or check valves in that backward flow is prevented by the closed diaphragm. Typical PEEP valve function depends on a valve that is closed by a spring (illustrated in FIGS. 1A and 1B). The spring can be manually tensioned to apply a set amount of pressure (e.g., 5 cm $H_2O$). At atmospheric pressures, the valve stays closed, and pressure accumulates below the valve when the pre-valve pressure is less than the pressure exerted by the tensioned spring (FIG. 1A). When the pre-valve pressure accumulates to the point of greater pressure than the tensioned spring exerts, the valve opens, and gas is vented until the pre-valve gas pressure is again below the setpoint (See FIG. 1i).

When a PEEP valve is placed in an inline enclosure as illustrated in FIGS. 2A, 2B, 3A and 3B, the PEEP valve may function at pressures other than local atmospheric pressure. In this setting, the setpoint of the PEEP valve becomes the sum of the pressure exerted by the spring and the pressure exerted by the gas pressure in the post-valve compartment of the enclosure. The valve will now open only when the pre-valve pressure is greater than the sum of both the pressure the spring is tensioned to and the post-valve gas pressure.

Figure 4:
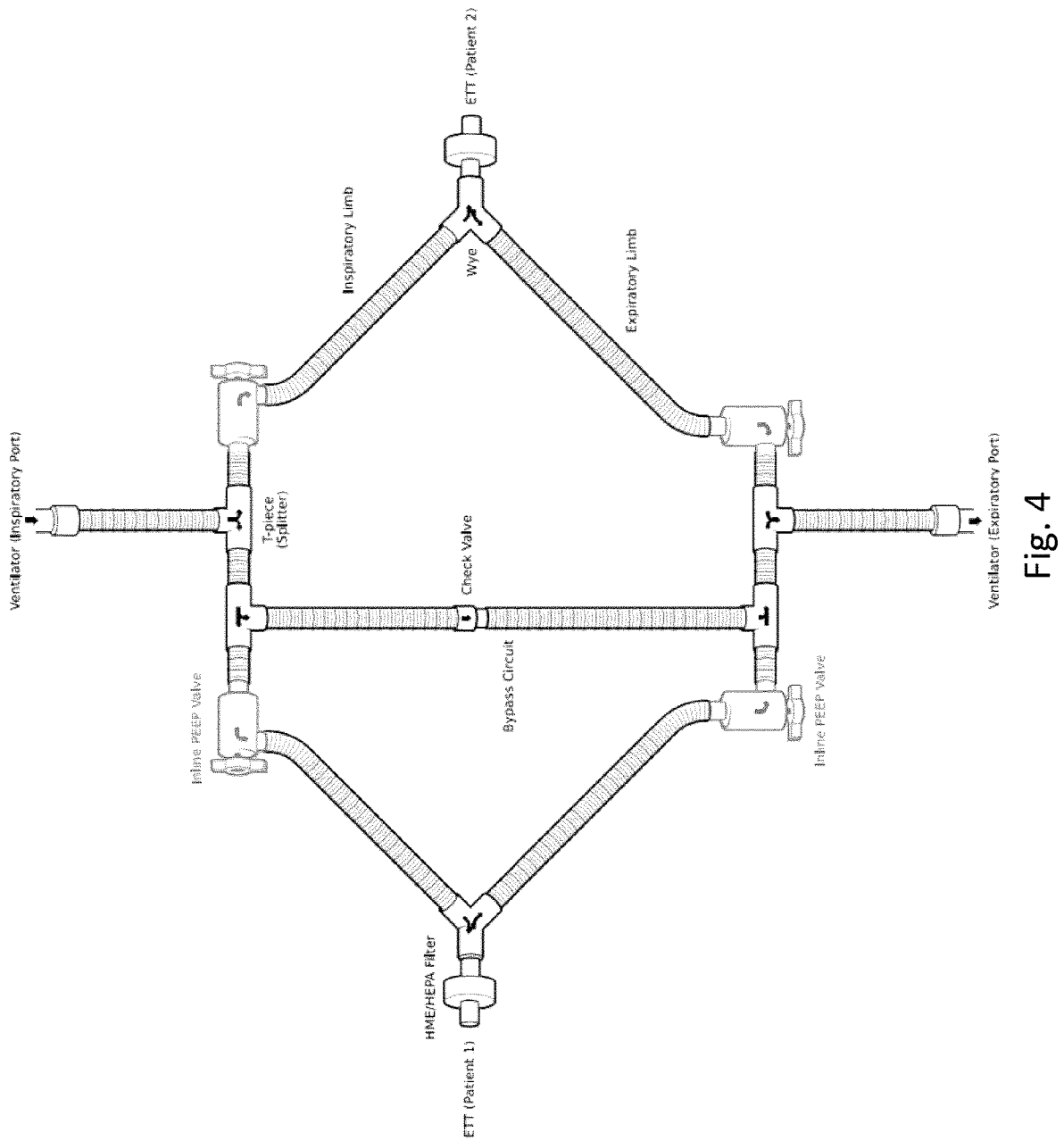
FIG. 4 is a diagram of an example of a simplified differential multi-ventilation circuit, in accordance with an aspect of the present invention.

Adjustable Inline PEEP Valves as Pressure Release Valves—When an inline PEEP valve is placed into the expiratory limb of a differential multi-ventilation system such as the system illustrated in FIG. 4, the gas entering the enclosure is expiratory flow from the patient, and post-valve gas pressure is regulated by the ventilator. Since post-valve gas pressure reflects the peak end expiratory pressure (PEEP) set on the ventilator, the additional resistance to flow out of the individual expiratory circuit by the spring represents additional PEEP above the PEEP set by the ventilator. Therefore, the inline PEEP valve setting in the expiratory circuit is additive to the ventilator PEEP (i.e. total PEEP is 10 cm $H_2O$ in a circuit when the inline PEEP valve is set to 5 cm $H_2O$ and the ventilator is set to maintain a PEEP of 5 cm $H_2O$).

Adjustable Inline PEEP Valves as Flow Restrictors—In contrast to the expiratory limb, use of inline PEEP valves in the inspiratory limb of a differential multi-ventilator circuit results in different behavior (FIGS. 3A and 3B). The gas entering the inlet of the enclosure is inspiratory flow from the ventilator, and the valve resists this flow with the tension in the spring. Pre-valve gas pressure reflects the peak inspiratory pressure (PIP) set on the ventilator, and the inline valve is tensioned with the requisite pressure drop needed to achieve the prescribed PIP for the individual patient ($PIP_{patient}$). At the beginning of the inspiratory phase, pressure in the individualized circuit should always be lower than the PIP pressure delivered by the ventilator ($PIP_{vent}$). Therefore, the valve will permit gas entry until the desired $PIP_{patient}$ is achieved. At this point, the post-valve gas pressure combined with the spring tension will equal or exceed the pre-valve pressure, and the valve will close. In this way, the inline PEEP valve setting in the inspiratory circuit is subtractive to the ventilator PIP (i.e., net $PIP_{patient}$ is 20 cm $H_2O$ in a circuit when the inspiratory inline valve is set to 5 cm $H_2O$, and the ventilator is set to deliver a $PIP_{vent}$ of 25 cm $H_2O$).

In contrast to the behavior of inline PEEP valves in the inspiratory circuit, most other types of flow restrictors that have been described for use in differential multi-ventilator systems provide much less predictable performance characteristics. For example, flow restrictors such as ball valves or pin valves rely on a variable constriction to create a flow limitation. This approach results in a consistent pressure drop only as long as the inspiratory time remains constant. When the inspiration/expiration ratio is changed such that the inspiratory time is prolonged, the pressure in the post-valve circuit has more time to equalize with the pre-valve pressure and can increase despite no change in the valve setting. In addition to the inspiratory time-dependent behavior, most valves have nonlinear flow restriction. In ball valves, for example, initial rotation of the control lever results in negligible changes in flow because the threshold constriction size has not been met. As the lever is further rotated and significant constriction occurs, smaller and smaller rotations of the lever result in larger and larger reductions in flow. Finally, ball valves and pin valves lack numerical settings in meaningful units, making reproduction or prediction of a required setting difficult. In contrast, adjustable inline PEEP valves do not suffer from these major drawbacks in differential multi-ventilator systems: PEEP valves demonstrate relatively time-independent behavior, near linear adjustable flow restriction, and do so with predictable numerical settings in the correct units (cm $H_2O$).

Check Valve Function of Inline PEEP Valves—In its basic construction, the PEEP valve is a spring-loaded disc check valve. As soon as the pressure on the outlet combined with the spring force exceeds the inlet pressure, the membrane will close the valve and the flow will stop. This check valve behavior ensures unidirectional flow in the individual patient circuits preventing rebreathing of expiratory gas. In differential multi-ventilator systems, every limb of a circuit requires a check valve. Therefore, when inline PEEP valves are used in the inspiratory and expiratory limbs of patient circuits, regular check-valves are only required in the bypass circuit (See FIG. 4).

Effects of Inline PEEP Valves On Ventilator Alarms—The use of inline PEEP valves should not significantly affect ventilator alarms in properly configured systems. In fact, the use of adjustable inline PEEP valves together with a bypass circuit specifically allows ventilator alarms to be left intact by ensuring two normal situations continue to occur at the expiratory port of the ventilator: equal net inspiratory and expiratory gas volume and equal gas pressure at the inspiratory and expiratory ventilator ports. Inline PEEP valves allow the creation of a closed system since, in contrast to traditional PEEP valves, no gas is vented to the atmosphere. Since inline PEEP valves should not introduce any leakage into the system when constructed with well-sealed materials, the volume of gas leaving the ventilator at the inspiratory circuit port is the same as the volume received at the expiratory port. This situation allows the ventilator to identify leaks when a discrepancy between the inspiratory and expiratory volume is detected and prevents false detection of patient respiratory effort which can result in ventilator auto cycling. In general, differential multi-ventilation systems using inline PEEP valves that have passed the ventilator self-check should not trigger "patient disconnect", "low pressure", or "low expiratory volume" alarms except when a disconnect event or new leak has occurred.

When inline PEEP valves are used in conjunction with a bypass circuit, the gas pressure at the expiratory port of the ventilator will be equal to $PIP_{vent}$ during inspiration and the ventilator-set PEEP during end-expiration. This situation is required to prevent "tube obstruction" and "high airway pressure" alarms whereby the ventilator detects inline PEEP valves as an obstruction. The bypass circuit is necessary when using inline PEEP valves with most ventilators not only to avoid triggering these alarms but also to maintain predictable behavior of the ventilator.

The foregoing description has established that inline PEEP valves which are housed within PEEP valve enclosures are important components of a differential multi-ventilator systems used for ventilating multiple patients with one ventilator. The present inventor is a member of the International Differential Multi-Ventilation Working Group and was among the first to recognize the utility of converting a conventional PEEP valve to an inline PEEP valve. One example of such an inline PEEP valve, (described in detail in Bunting et al. *Am. J. Emerg. Med.*, 2020, https://doi.org/10.1016/j.ajem.2020.06.089, incorporated herein by reference in its entirety) is constructed by providing a standard PEEP valve with a 3D-printed collar and an outlet which is coupled to upper ports of the PEEP valve to collect the expiratory flow from the PEEP valve and direct it to the ventilator. Another example of a structure for converting a conventional PEEP valve to an inline PEEP valve is the enclosure shown in FIG. 3C in Roy et al, 2020, *Crit. Care Explor.* 2(9): e0198, incorporated herein by reference in its entirety, where the PEEP valve is completely encased in a plastic enclosure having an air input port, an air output port and a valve pressure adjuster coupled to the PEEP valve and extending out of the enclosure.

In considering alternative structures of PEEP valve enclosures for constructing inline PEEP valves, the present inventor discovered that PEEP valve enclosures can be adapted to provide additional functionality for significantly improving the construction of differential multi-ventilator systems and providing them with arrangements which are easily accessed and manipulated for the purpose operating a differential multi-ventilator system and extending it without halting its operation, thereby allowing patients to continue to be ventilated.

In one aspect, it was discovered that the PEEP valve enclosure could be constructed with a third connector arm port to permit the constructed inline PEEP valve to function as a splitter to extend a conduit for assembly of an additional patient circuit. Provided that the additional patient circuit also included similar inline PEEP valves with the same splitter feature, a further patient circuit could then be added to the previously added patient circuit and the process could then be continued. In conferring this adaptability, a number of additional useful functional features were discovered. These features are described hereinbelow in context of an example embodiment and various alternatives with reference to FIGS. 5 to 12.

For the purposes of illustration, components depicted in the figures are not necessarily drawn to scale in all cases. Instead, emphasis is placed on highlighting the various contributions of the components to the functionality of various aspects of the technology. A number of possible alternative features are introduced during the course of this description. It is to be understood that, according to the knowledge and judgment of persons skilled in the art, such alternative features may be substituted in various combinations to arrive at different embodiments of the present technology.

Figures 5, 6:
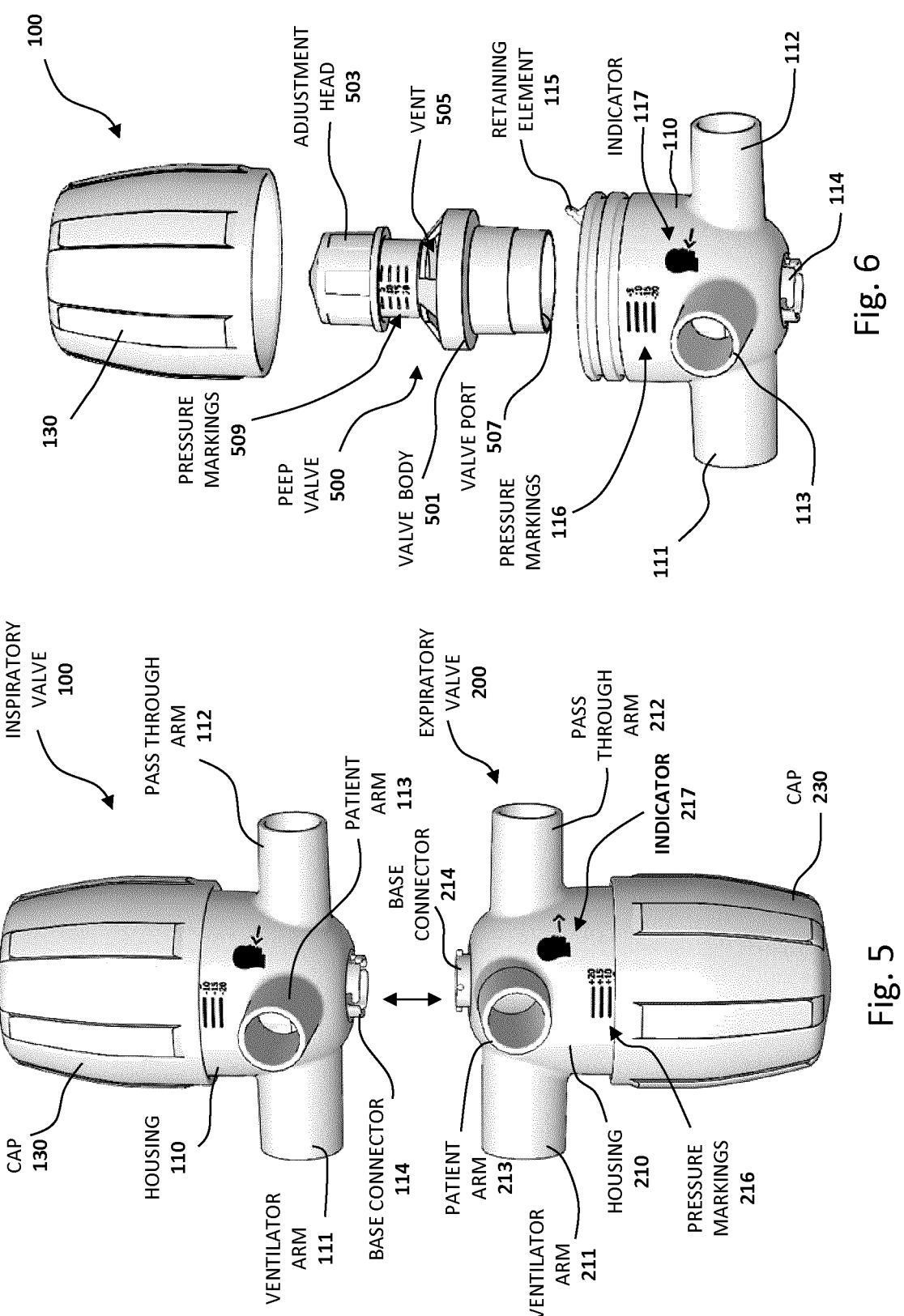
FIG. 5 is a set of inline valves shown in different perspective views including an inspiratory valve 100 and expiratory valve 200, in accordance with an aspect of the present invention.
FIG. 6 is an exploded perspective view of an inspiratory inline valve 100 which includes a PEEP valve 500, in accordance with an aspect of the present invention.

Devices for Constructing Inline Valves using PEEP Valves—With reference to FIGS. 5 to 10, example embodiments of devices for constructing inline valves by incorporating PEEP valves are shown. The term "PEEP valve" is used to refer to conventional commercially available valves having a structure similar to the structures illustrated in FIGS. 1A and 1B. However, as used herein the PEEP valve is converted into an inline valve used within an inspiratory circuit and within an expiratory circuit. Therefore, in the case of the inspiratory circuit, the PEEP valve within the inspiratory inline valve operates as a peak inspiratory pressure (PIP) valve. Nonetheless, to avoid confusion, the term PEEP valve is used throughout the ensuing description to refer to a valve having the features illustrated in FIGS. 1A and 1B because the same PEEP valve is used in the inspiratory inline valve and the expiratory inline valve. FIG. 5 shows an inspiratory valve 100 and an expiratory valve 200. The inline valves 100 and 200 are generally of similar construction with a few exceptions. One notable exception which can be seen in FIG. 5 is that the inline valves 100 and 200 are mirror images of each other with respect to a mirror plane passing between the base connectors 114 and 214. Therefore, if the inline expiratory valve 200 is rotated to provide it with the same orientation as the inline inspiratory valve 100, the ventilator-side arm 211 of the expiratory inline valve 200 would be located on the right side and the pass-through arm 212 would be located on the left side. There are additional exceptions which will be described hereinbelow. To simplify the ensuing description, the features of the devices used to form the inline valves 100 and 200 will be described with respect of the inspiratory valve 100 and exceptions in construction of the expiratory valve 200 will be described in turn when features representing exceptions are introduced.

Figure 7:
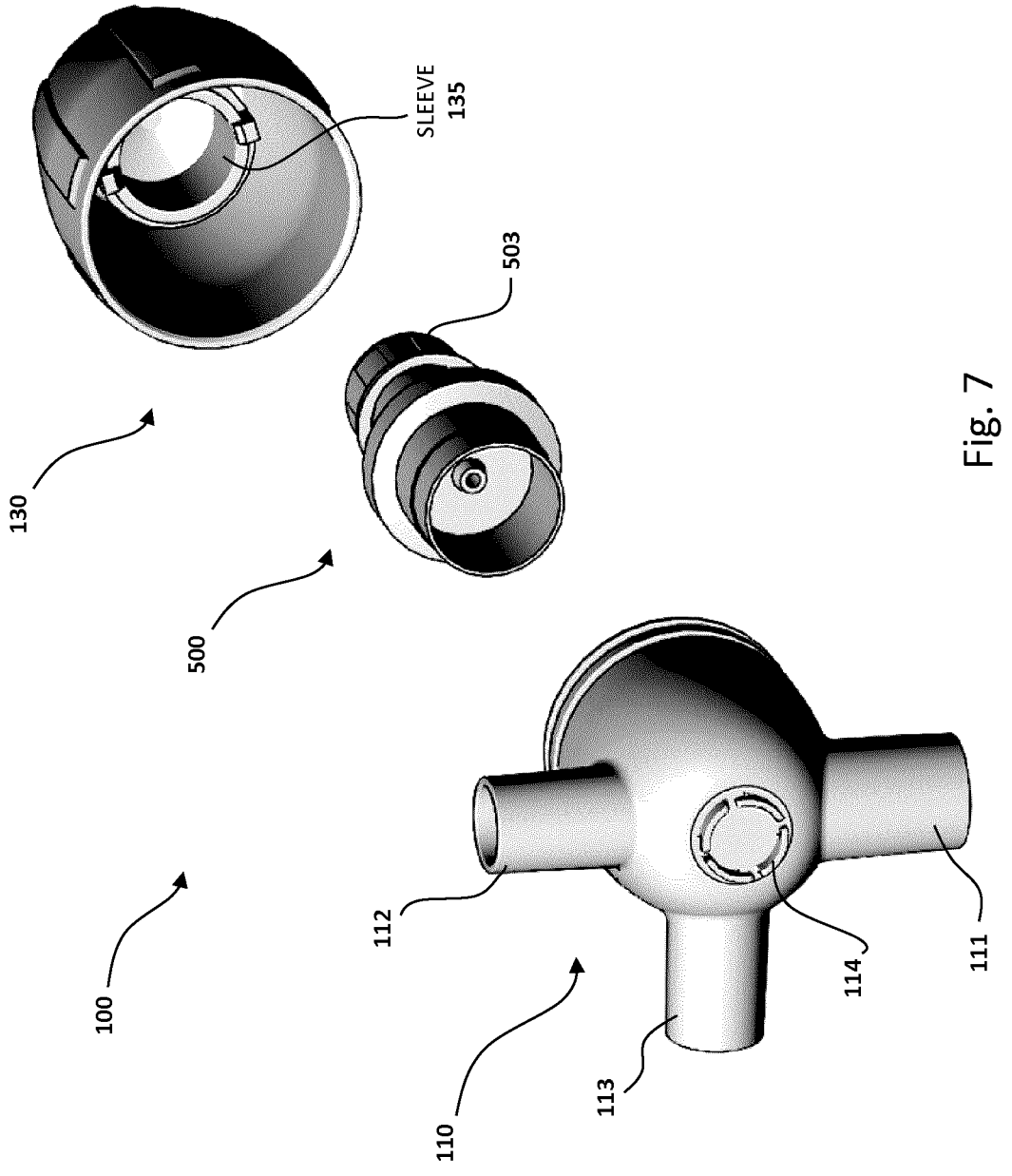
FIG. 7 is another exploded perspective view of inspiratory inline valve 100 which includes PEEP valve 500, in accordance with an aspect of the present invention.

It is seen in the exploded views of FIGS. 6 and 7 that the inspiratory device for valve 100 includes a housing 110 and a cap 130 and likewise the expiratory device for inline valve 200 includes a housing 210 and a cap 230. The inspiratory device and the expiratory device are each configured to hold a conventional PEEP valve 500 and convert the PEEP valve 500 to either an inline inspiratory valve 100 or inline expiratory valve 200. Thus, it is to be understood that the PEEP valve 500 itself is not to be considered part of the inspiratory device or the expiratory device. It is seen in FIG. 6 that the PEEP valve 500 includes a valve body 501, with a pressure adjustment head 503, a series of vents 505 and a main valve port 507. The pressure adjustment head 503 is twisted to adjust the pressure required to counteract the inner valve spring (not shown) to open the PEEP valve 500 where the flowing gas exits the PEEP valve 500 via the vents 505.

Figure 11:
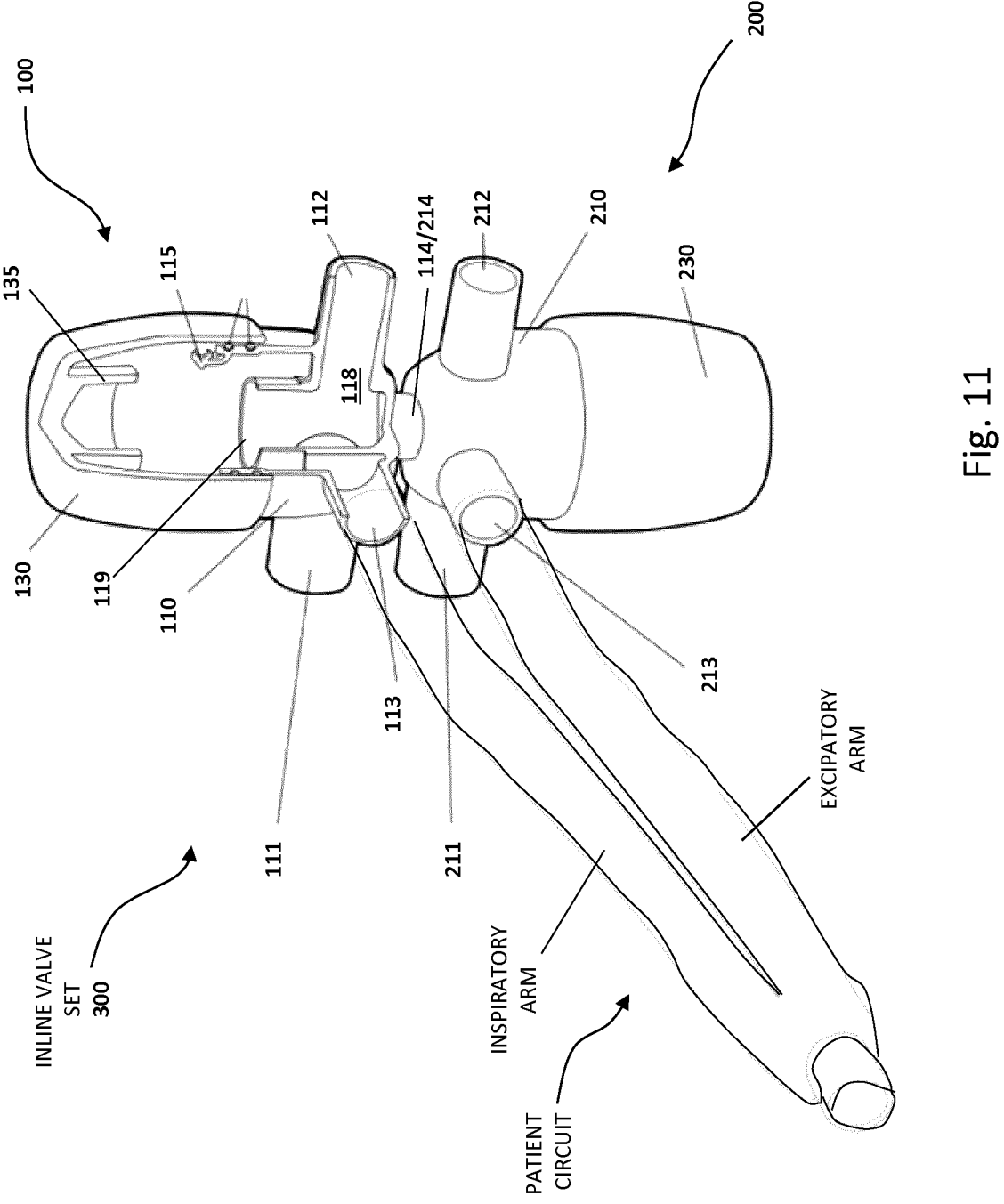
FIG. 11 is a perspective view of a connected set of inline valves including inspiratory valve 100 and expiratory valve 200 connected via base connectors 114 and 214, in accordance with an aspect of the present invention.
Figure 12:
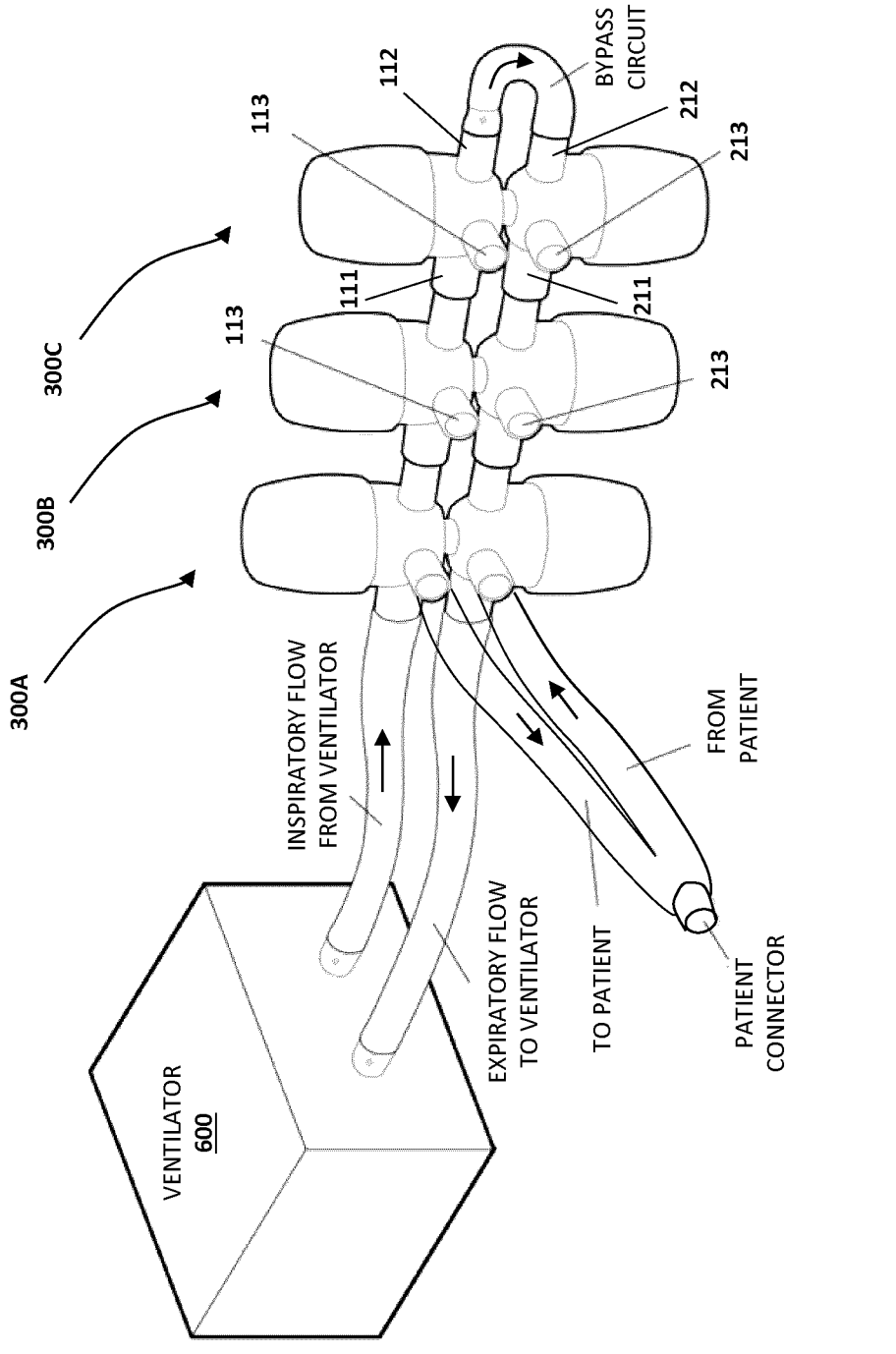
FIG. 12 is perspective view of a differential multi-ventilator system showing three sets of connected inline valves 300A-C connected to a ventilator 600, in accordance with an aspect of the present invention.

In this particular embodiment, the housing 110 of the inspiratory valve 100 is formed by injection molding or additive manufacturing to include a ventilator-side arm 111, a co-axial pass-through arm 112, a patient arm 113 and a base connector 114. Likewise, the housing 210 of the inspiratory valve 200 is formed by injection molding or additive manufacturing to include a ventilator-side arm 211, a co-axial pass-through arm 212, a patient arm 213 and a base connector 214. In comparing the base connectors 114 and 214, it can be seen that the connectors are complementary, for the purpose of connecting the inspiratory valve 100 to the expiratory valve 200 as illustrated in FIGS. 11 and 12. In this embodiment, base connector 214 includes pegs which fit into slots of the base connector 114 in a conventional quick-connect arrangement. Alternative embodiments may use other types of connectors. Advantageously the connected inline valves 100 and 200 form a rigid set which is resistant to inadvertent disconnection.

Figures 8, 9, 10:
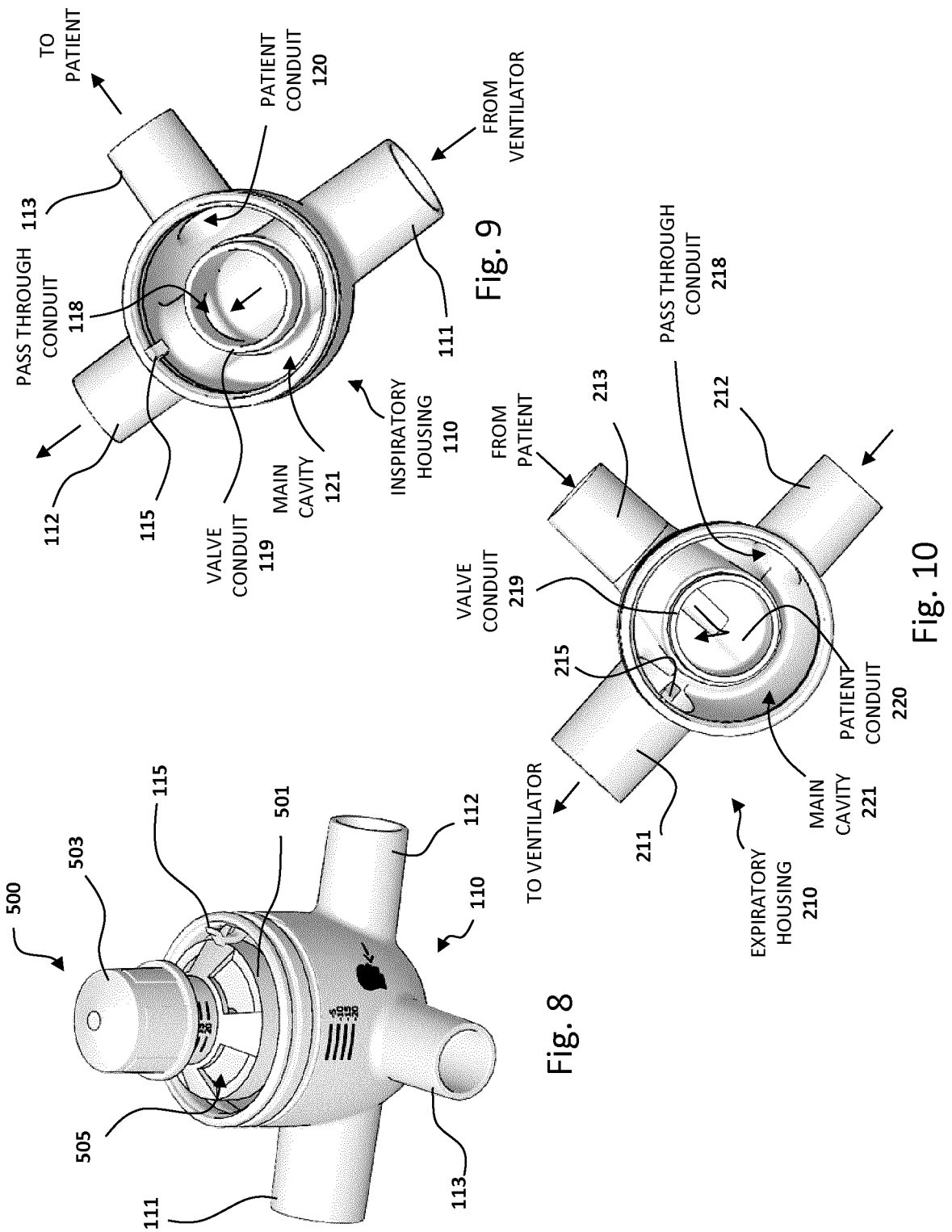
FIG. 8 is a perspective view of the PEEP valve 500 installed in the housing 110, in accordance with an aspect of the present invention.
FIG. 9 is a top perspective view of the inspiratory housing 110, in accordance with an aspect of the present invention.
FIG. 10 is a side elevation view of the expiratory housing 210, in accordance with an aspect of the present invention.

The housing 110 is provided with a retaining element 115 which holds the PEEP valve 500 in place within the housing 110 (See FIG. 8). In this embodiment the retaining element 115 is in the form of a clip integrally formed with the housing 110, which is bendable and biased inwards towards the center of the housing 110. Alternatively, the retaining element may be a separate part which is fixed to the inside of the housing 110. FIG. 8 illustrates how the retaining element 115 engages the valve body 501 of the PEEP valve 500 to hold it in place. To install the PEEP valve 500, the retaining element is manually bent outward and held while the PEEP valve 500 is placed in the housing 110 and then the retaining element 115 is released to permit its biased orientation to exert a force against the valve body 501 of the PEEP valve 500.

Because the PEEP valve 500 is enclosed within the inspiratory valve 100, pressure markings 116 are provided on the outer sidewall of housing 110 of the inspiratory valve 100. These pressure markings 116 (indicating conventional units of cm of $H_2O$) are positioned with calibration to match the pressure markings 509 of the PEEP valve 500. The cap 130 engages the pressure adjustment head 503 of the PEEP valve 500 via a sleeve 135 extending from the flat upper surface of the cap 130 (see FIG. 7). By turning the cap 130 which is threaded to the housing 110, the cap 130 causes the pressure adjustment head 503 to twist to adjust the spring tension of the PEEP valve 500 such that the pressure value indicated at the bottom edge of the cap 130 represents the pressure setting of the PEEP valve 500. The housing 210 of the expiratory valve 200 also includes pressure markings 216 and the cap 230 operates with the pressure adjustment head 503 of the PEEP valve 500 enclosed therein in a similar manner. This same arrangement operates in the expiratory valve 200 with the cap 230 causing the pressure adjustment head 503 to twist to adjust the spring tension of the PEEP valve 500.

In some embodiments, one or more components of the enclosure (for example, the base, the cap, or both) are made with a transparent material in to allow the setting gradations on the commercial PEEP valve to be read from outside the enclosure. This eliminates the need for calibrated external lines to be printed or embossed on the outside of the device.

The outer sidewall of the housing 110 is also provided by a graphic indicator 117 (in this embodiment a human head with an arrow indicating inspiration) to designate that the housing 110 is for the inspiratory valve 100. Likewise housing 210 includes a graphic indicator 217 (in this embodiment a human head with an arrow indicating expiration) to designate that the housing 210 is for the expiratory valve 200. In this manner, the two different inline valves 100 and 200 can be easily distinguished so that pressure setting errors can be conveniently avoided. Because the expiratory valve 200 is intended to be used in an inverted orientation relative to the inspiratory valve 100, the pressure markings 216 and the graphic indicator 217 are oriented accordingly such that when the inspiratory valve 100 and the expiratory valve 200 are connected to each other via their base connectors 114 and 214, the pressure markings 116 and 216 and the graphic indicators 117 and 217 are properly oriented for convenient identification.

The threading of the caps 130 and 230 to the housing may be arranged in a conventional manner to affect an increase in valve pressure with clockwise rotation of the caps 130 and 230.

Turning now to FIGS. 9 and 10, the interior structures of the inspiratory housing 110 and the expiratory housing 210 are shown to indicate differences between them in terms of valve and conduit arrangements with respect to the main cavities 121 and 221 of the housings 110 and 210. In the inspiratory housing (FIG. 9), the ventilator-side arm 111 is co-axial and contiguous with the pass-through arm 112 such that gas entering from the ventilator via the port in the ventilator-side arm 111 passes through the housing 110 and exits the pass-through arm 112, as well as being contiguous with a valve conduit 119 which extends upward from the center of the main cavity 121 of the housing 110 in the orientation shown. While not specifically shown in FIG. 9, it is to be understood that the valve port 507 of the PEEP valve 500 connects to the valve conduit 119 of the housing 110. Therefore, gas flowing from the ventilator (providing inspiration) into the valve conduit 119 will exert pressure upon the PEEP valve 500. If the inspiratory pressure is sufficient to counteract the set pressure of the PEEP valve 500, the gas will exit the PEEP valve 500 through vents 505 in the PEEP valve, enter the main cavity 121 of the housing 110 and exit the main cavity 121 via the patient conduit 120 which extends outward via the patient arm 113. In the expiratory housing 210 (FIG. 10), the direction of gas flow is reversed relative to the direction of gas flow described above for the inspiratory housing 110. The ventilator-side arm 211 and the pass-through arm 212 are contiguous with the main cavity 221. The patient conduit 220 extending from the patient-side arm 213 is contiguous with the valve conduit 219. While not specifically shown in the FIG. 10, it is to be understood that the valve port 507 of the PEEP valve 500 connects to the valve conduit 219 of the housing 210. Therefore, gas flowing from the patient (expiration) into the valve conduit 219 will exert pressure upon the PEEP valve 500 (not shown in FIG. 10). If the expiratory pressure is sufficient to counteract the set pressure of the PEEP valve 500, the gas will exit the PEEP valve 500 through vents 505 in the PEEP valve and enter the main cavity 221 of the housing 210 and exit the main cavity 221 via the ventilator-side arm 211 which extends to the ventilator.

Differential Multi-Ventilator Systems and Methods of Assembly—FIGS. 11 and 12 show how an inline valve set 300 comprised of connected inline valves 100 and 200 can be connected to a patient circuit and used to construct a differential multi-ventilator system. FIG. 11 shows a patient circuit with an inspiratory arm connected to the patient arm 113 of the inspiratory valve 100 and an expiratory arm connected to the patient arm 213 of the expiratory valve 200.

FIG. 12 shows the same arrangement in an extended series which includes conduits connecting a first inline valve set 300A to a ventilator 600 and a second inline valve set 300B with its ventilator-side arms 111 and 211 connected to the pass-through arms 112 and 212 of the first inline valve set 300A. Likewise, a third inline valve set 300C is connected via its ventilator-side arms 111 and 211 to the pass-through arms 112 and 212 of the second inline valve set 300B. A bypass circuit is connected to the pass-through arms 112 and 212 of the third inline valve set 300C.

It is to be understood that if it is desired to extend the series of inline valve sets to include a fourth set of inline valves (not shown), this extension can be accomplished in a convenient manner without disconnecting any of the patient circuits which may already be in place and in operation serving connected patients with ventilation. The addition of a fourth set of inline valves is accomplished simply by disconnecting the bypass circuit from the pass-through arms 112 and 212 of the third inline valve set 300C and then connecting ventilator-side arms 111 and 211 of a fourth inline valve set (not shown) to the pass-through arms 112 and 212 of the third inline valve set 300C, followed by installation of the bypass circuit on the pass-through arms 112 and 212 of the fourth inline valve set. If the ventilator 600 is operating during this procedure, ventilator alarms will sound after the bypass circuit is removed from the third inline valve set 300C but since the addition of a fourth inline valve set may be accomplished quickly in less than about 20 seconds, followed by installation of the bypass circuit to the pass-through arms 112 and 212 of the fourth inline valve set, the alarms will not be of concern and patients connected to the differential multi-ventilator system via the first, second or third inline valve sets 300A-C, will not be impacted to any considerable extent. Therefore, a differential multi-ventilator system constructed using the inspiratory and expiratory devices described herein provides a convenient way to extend the system with no significant disruption to patients receiving ventilation from the system.

Kits for Constructing Differential Multi-Ventilator Systems—One aspect of the technology is a commercial kit for converting conventional PEEP valves to inline valves for installation in a differential multi-ventilator system. In one embodiment, the kit includes a set of devices with each device of the set including a housing configured to enclose the PEEP valve, the housing including a ventilator-side arm, a pass-through arm and a patient-side arm, the pass-through arm permitting extension of the multi-ventilation system to add one or more circuits to the system. In other embodiments the kit includes a set of devices as described with respect to FIG. 5. In some embodiments, the kit includes instructions for assembly of a differential multi-ventilator system. The instructions may include details of the method for assembly of a differential multi-ventilator system which is described above. In some embodiments the kit includes a plurality of PEEP valves. In an alternative embodiment, a differential multi-ventilator system may be assembled either with 2 T-pieces (splitters) at the ventilator-side to place the bypass circuit at that location. In this case, plugs would be installed at the terminal pass-through arms of the terminal valve set. Adding an additional valve set would involve removing the plugs and connecting the ventilator-side arms of the additional valve set to the pass-through arms of the previous terminal valve set, followed by installation of the plugs on the pass-through arms of the added valve set.

Some alternative embodiments have a housing with one or more arms provided with a built-in self-closing push in connector which could prevent the ventilator from sounding alarms when new valve sets are added to the differential multi-ventilator system.

Some alternative embodiments may have the housings with connectors mounted in different locations on the housings. In one such embodiment, the connectors are formed in or mounted to the sidewall of the housings at positions opposite the patient-side arms so that the housings are connected in a back-to-back arrangement instead of the base-to-base arrangement shown in FIGS. 11 and 12.

In some alternative embodiments, the pressure adjustment head of the PEEP valve is removed and the spring of the spring valve is compressed directly via operation of the cap of the inline valve.

In some alternative embodiments, the ventilator may be arranged at the opposing end relative to the arrangement illustrated in FIG. 12 or arranged between adjacent inline valve sets with provision of suitable T-splitters.

Advantages—Embodiments of the inline inspiratory and expiratory devices described herein have a number of advantages. They minimize superfluous volume, have minimal parts, can be manufactured conveniently by additive manufacturing or injection molding, are easy to disassemble for cleaning, disinfection and sterilization, and have a compact structure to minimize storage requirements. Furthermore, while designed to be used in equal number to number of patients (i.e., n) can also be used in combination with 2 check-valves in an N−1 setup. This would allow a single unit to split a ventilator between two patients (the inspiratory circuit with the lower PIP is connected to the unit in the usual fashion as is the expiratory circuit with the higher PEEP. The other two circuit are connected to the pass-through with a check valve.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art to which this technology belongs.

While this technology has been particularly shown and described with references to embodiments thereof, it will be understood by those skilled in the art that various changes in form and details may be made therein without departing from the scope of the technology encompassed by the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

It is also noted that the term "comprising" is intended to be open and permits but does not require the inclusion of additional elements or steps. When the term "comprising" is used herein, the term "consisting of" is thus also encompassed and disclosed. Where ranges are given, endpoints are included. It is to be understood that any particular embodiment of the present technology that falls within the prior art may be explicitly excluded from any one or more of the claims. Since such embodiments are deemed to be known to one of ordinary skill in the art, they may be excluded even if the exclusion is not set forth explicitly herein.

What is claimed is:

1. A device for enclosing a positive end valve (PEEP valve) and converting the PEEP valve to an inline valve for use in a differential multi-ventilation system, the device comprising:
a housing configured to enclose the PEEP valve, the housing including a ventilator-side arm, a pass-through arm and a patient-side arm,
wherein the device is configured such that, when the PEEP valve is installed:
gas flow is permitted between the ventilator-side arm and the pass-through arm;
the ventilator-side arm and the pass-through arm are isolated from the patient-side arm by the PEEP valve when the PEEP valve is closed;
gas flow between the patient-side arm and the ventilator-side arm is permitted when the PEEP valve is open; and
the pass-through arm is configured to permit extension of the multi-ventilation system to add one or more patient circuits to the system.

2. The device of claim 1, wherein the ventilator-side arm and the pass-through arm are dimensioned for direct connection to each other such that the pass-through arm of a first device as recited in claim 1 is connectable to the ventilator-side arm of a second device, wherein the second device has the same features as the first device.

3. The device of claim 1, wherein the device is configured for use as an inspiratory inline valve, wherein the ventilator-side arm together with the pass-through arm are co-axial with a first conduit through the housing, the first conduit contiguous with a substantially perpendicular second conduit substantially centralized within the housing, the second conduit configured to connect to a valve port of the PEEP valve when the PEEP valve is installed in the device.

4. The device of claim 3, wherein the second conduit is isolated from the patient-side arm when the PEEP valve is installed in the device and the PEEP valve is closed, and wherein the second conduit permits gas flow to the patient-side arm when the PEEP valve is installed in the device and the PEEP valve is open.

5. The device of claim 1, wherein the device is configured for use as an expiratory inline valve, wherein the patient-side arm is contiguous with a substantially perpendicular second conduit substantially centralized within the housing, the second conduit configured to connect to a main sleeve of the PEEP valve when the PEEP valve is installed in the device.

6. The device of claim 5, wherein the second conduit is isolated from the ventilator-side arm and the pass-through arm when the PEEP valve is installed in the device and the PEEP valve is closed, and wherein the second conduit permits gas flow to the ventilator-side arm when the PEEP valve is installed in the device and the PEEP valve is open.

7. The device of claim 1, wherein the housing comprising a main opening and a cap is coupled to the body over the main opening, the cap having an inner structure configured to connect to a pressure adjustment head of the PEEP valve, thereby permitting the cap to control the pressure adjustment head of the PEEP valve.

8. The device of claim 7, wherein the inner structure of the cap is a sleeve dimensioned to couple to the pressure adjustment head of the PEEP valve when the PEEP valve is installed in the device.

9. The device of claim 7, wherein the cap is coupled to the housing by threading, wherein the threading permits adjustment of the pressure adjustment head of the PEEP valve.

10. The device of claim 9, wherein an outer sidewall of the housing includes markings indicating valve pressure, wherein positioning of an edge of the cap with respect to the markings indicates the valve pressure according to a position relative to the threading.

11. The device of claim 1, wherein an inner sidewall of the housing includes a PEEP-valve retaining element.

12. The device of claim 1, wherein the PEEP valve is a check valve.

13. A set of devices for assembling and connecting inspiratory and expiratory inline valves to each other, the set for use in a differential multi-ventilation system, the set comprising:

an inspiratory device comprising:

a housing configured to enclose a positive end valve (PEEP valve), the housing including a ventilator-side arm, a pass-through arm and a patient-side arm, wherein the inspiratory device is configured such that, when the PEEP valve is installed:

gas flow is permitted between the ventilator-side arm and the pass-through arm in either direction, the ventilator-side arm and the pass-through arm are isolated from the patient-side arm by the PEEP valve when the PEEP valve is closed, gas flow from the ventilator-side arm to the patient side arm is permitted when the PEEP valve is open, and the pass-through arm is configured to permit extension of the multi-ventilation system to add one or more patient circuits to the system, and further including: a first connector on the housing of the inspiratory device; and an expiratory device comprising:

a housing configured to enclose a PEEP valve, the housing including a ventilator-side arm, a pass-through arm and a patient-side arm, wherein the expiratory device is configured such that, when the PEEP valve is installed;

gas flow is permitted to flow between the ventilator-side arm and the pass-through arm in either direction, the ventilator-side arm and the pass-through arm are isolated from the patient-side arm by the PEEP valve when the PEEP valve is closed, gas flow from the patient side arm to the ventilator-side arm is permitted when the PEEP valve is open, and the pass-through arm is configured to permit extension of the multi-ventilation system to add one or more patient circuits to the system, and further including: a second connector on the housing of the expiratory device, wherein the first connector and the second connector are configured to connect to each other.

14. The set of devices of claim 13, wherein the housing of the inspiratory device includes a first visual indicator to indicate inspiration and the housing of the expiratory device includes a second visual indicator to indicate expiration.

15. A kit comprising the set of devices of claim 13, the kit further comprising instructions for assembling a differential multi-ventilator system using the set of devices.

16. The kit of claim 15, further comprising a plurality of PEEP valves.

17. A ventilator system comprising:

a ventilator and a set of inline valves formed from devices as recited in claim 13 having PEEP valves installed therein, wherein the ventilator-side arms of both the inspiratory device and the expiratory device are connected to the ventilator, the patient-side arms of both the inspiratory device and the expiratory device are connected to a first patient circuit, and a bypass conduit is connected between the pass-through arms of the inspiratory device and the expiratory device.

18. A differential multi-ventilator system comprising:

a ventilator and a first set of inline valves formed from devices as recited in claim 13 having PEEP valves installed therein, wherein the ventilator-side arms of both the inspiratory device and the expiratory device of the first set of inline valves are connected to the ventilator, and the patient-side arms of both the inspiratory device and the expiratory device of the first set of inline valves are connected to a first patient circuit;

a second set of inline valves formed from devices as recited in claim 13 having PEEP valves installed therein, the second set of inline valves connected to the first set of inline valves, wherein the pass-through arms of the inspiratory device and the expiratory device of the first set of inline valves are connected to the ventilator-side arms of the inspiratory device and the expiratory device of the second set of inline valves and the patient-side arms of both the inspiratory device and the expiratory device of the second set of inline valves are connected to at least a second patient; and a bypass conduit is connected between the pass-through arms of the second set of inline valves or connected between the pass-through arms of a final set of inline valves connected after the second set of devices.

19. The method of claim 18, wherein the ventilator is retained in continuous operation and the first patient circuit continues to operate during the step of connecting at least a second set of inline valves.

20. A method for assembling a differential multi-ventilator system, the method comprising:

constructing a plurality of sets of inline valves by installing PEEP valves in a plurality of inspiratory devices and expiratory devices as recited in claim 13;

connecting a first set of inline valves of the plurality of inline valves to a ventilator via the ventilator-side arm of the inspiratory device and the ventilator-side arm of the expiratory device of the first set of devices and connecting a first patient circuit to the patient-side arms of the first set of inline valves;

connecting at least a second set of inline valves to the first set of inline valves by connecting the pass-through arm of the inspiratory device of the first set of inline valves to the ventilator-side arm of the second set of inline valves and connecting at least a second patient circuit to the patient-side arms of the second set of inline valves; thereby providing an extended set of inline valves; and connecting a bypass conduit between the pass-through arms of a final set of inline valves in the extended set of inline valves.

21. The method of claim 20, wherein the extended set of inline valves comprises at least one of 2, 3, 4, 5 or 6 sets of inline valves.

22. The method of claim 20, wherein for each set of inline valves of the extended set of inline valves, the inspiratory device is connected to the expiratory device by making a connection between the first connector and the second connector.

23. The method of claim 20, further comprising removing the bypass conduit from the final set of inline valves, connecting an additional set of inline valves to the final set of inline valves and connecting the bypass conduit between the pass-through arms of the additional set of inline valves, thereby adding the additional set of inline valves to the extended set of inline valves.

\* \* \* \* \*